(12) United States Patent
Luo et al.

(10) Patent No.: US 7,509,163 B1
(45) Date of Patent: Mar. 24, 2009

(54) METHOD AND SYSTEM FOR SUBJECT-ADAPTIVE REAL-TIME SLEEP STAGE CLASSIFICATION

(75) Inventors: Gang Luo, Yorktown Heights, NY (US); Wanli Min, Mount Kisco, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 11/863,586

(22) Filed: Sep. 28, 2007

(51) Int. Cl.
*A61B 5/05* (2006.01)

(52) U.S. Cl. .................................... 600/544
(58) Field of Classification Search ................ 600/544, 600/545
See application file for complete search history.

(56) References Cited

U.S. PATENT DOCUMENTS 5,320,109 A * 6/1994 Chamoun et al. ........... 600/544
6,419,629 B1 * 7/2002 Balkin et al. ................ 600/300
7,299,088 B1 * 11/2007 Thakor et al. ............... 600/544
2006/0085190 A1 * 4/2006 Gunawardana et al. .. 704/256.3

* cited by examiner

*Primary Examiner*—Charles A Marmor, II
*Assistant Examiner*—Christian Y Jang
(74) *Attorney, Agent, or Firm*—McGinn IP Law Group, PLLC; Stephen C. Kaufman, Esq.

(57) ABSTRACT

A method of subject-adaptive, real-time sleep stage classification to classify electroencephalogram sleep recordings into sleep stages to determine whether a subject exhibits a sleep disorder includes performing subject adaptation to improve classification accuracy for a new subject with limited training data, the performing subject adaptation comprises using linear-chain conditional random fields and potential functions, training the linear-chain conditional random fields using the training data, continuously receiving the electroencephalogram waves, continuously extracting features from the electroencephalogram waves, the extracting features comprising transforming each of the electroencephalogram waves to capture information embedded in the electroencephalogram waves, and continuously classifying the sleep stages according to extracted features and learned parameters from the linear-chain conditional random fields.

1 Claim, 2 Drawing Sheets

METHOD AND SYSTEM FOR SUBJECT-ADAPTIVE REAL-TIME SLEEP STAGE CLASSIFICATION

BACKGROUND OF THE INVENTION

1. Field of the Invention

The present invention generally relates to a method and apparatus for classifying sleep recordings, and more particularly to a method and apparatus for classifying electroencephalogram sleep recordings into sleep stages using conditional random fields and subject adaptation.

2. Description of the Related Art

Sleep is indispensable to everybody. About one-third of Americans exhibit some kind of sleep problem. Hence, the study of sleep patterns, much of which is through sleep recordings, has consistently been an important research topic.

A typical sleep recording has one or more channels of electroencephalogram (EEG) waves coming from electrodes. Sleep staging is the pattern recognition task of classifying sleep recordings into sleep stages (e.g., wake, sleep) continuously. This task is crucial for the diagnosis and treatment of various sleep disorders. In addition, it relates closely to brain-machine interfaces, where successful classification can facilitate disabled people to control computers. Sleep staging is also of special interest to the study of avian bird song system and the evolutionary theory of mammalian sleep.

Many statistical pattern recognition methods, such as autoregression, and hidden Markov model (HMM), have been used to build an automatic, online sleep stager. Despite all these efforts, existing sleep stagers can only achieve average classification accuracy below 80%, which is insufficient for physicians to diagnose sleep disorders correctly. (In brain-computer interfaces, incorrect EEG wave classification can cause computers to receive wrong instructions.)

SUMMARY OF THE INVENTION

In view of the foregoing and other exemplary problems, drawbacks, and disadvantages of the conventional methods and structures, an exemplary feature of the present invention is to provide a method and system that can continuously classify electroencephalogram sleep recordings into sleep stages (e.g., wake, sleep) with improved classification accuracy.

In a first aspect of the present invention, a method of subject-adaptive, real-time sleep stage classification to classify electroencephalogram sleep recordings into sleep stages to determine whether a subject exhibits a sleep disorder includes performing subject adaptation to improve classification accuracy for a new subject with limited training data, the performing subject adaptation comprises using linear-chain conditional random fields and potential functions, training the linear-chain conditional random fields using the training data, continuously receiving the electroencephalogram waves, continuously extracting features from the electroencephalogram waves, the extracting features comprising transforming each of the electroencephalogram waves to capture information embedded in the electroencephalogram waves, and continuously classifying the sleep stages according to extracted features and learned parameters from the linear-chain conditional random fields. The performing subject adaptation includes using training data from a plurality of old subjects to obtain a prior distribution of conditional random field parameters, using the prior distribution of conditional random field parameters in combination with training data for at least one new subject to obtain a regulated estimate of conditional random field parameters, and using the regulated estimate of conditional random field parameters to classify the electroencephalogram waves of the at least one new subject to determine whether a subject exhibits a sleep disorder.

The present method (and system) provides an automatic, online sleep stager based on a recently developed statistical pattern recognition method, conditional random field (CRF), and novel potential functions that have explicit physical meanings. The sleep stager's classification accuracy is much higher than that of existing methods.

One challenge for sleep staging is that in practice, there is often enough training data $D_{old}$ from several old subjects $s_{old}$ but very limited training data $D_{new}$ from a new subject $s_{new}$, as it often takes several days or several weeks to label sufficient $D_{new}$ for $s_{new}$ manually. In this case, it is undesirable to train the parameter vector $\Theta$ of the CRF by only using $D_{new}$.

The present invention, however, may perform subject adaptation to improve the classification accuracy on $s_{new}$. The present invention uses the knowledge on $\Theta$ that is learned from $D_{old}$ to obtain a regulated estimate of $\Theta$ from $D_{new}$. In this way, the classification accuracy on $s_{new}$ increases with the size of $D_{new}$ and eventually becomes close to the theoretical limit. Especially, even without any $D_{new}$, the average accuracy on $s_{new}$ can be quite good.

CRF was originally proposed by the natural language processing community in 2001 and has been successfully applied to pattern recognition tasks in computer vision. In contrary to HMM, CRF directly models the probabilities of possible label sequences given an observation sequence, without making unnecessary independence assumptions on the observation elements. Consequently, CRF overcomes HMM's shortcoming of being unable to represent multiple interacting features or long-range dependencies among the observation elements. Neither the application of CRF nor subject adaptation has been studied before in EEG wave classification.

BRIEF DESCRIPTION OF THE DRAWINGS

The foregoing and other exemplary purposes, aspects and advantages will be better understood from the following detailed description of an exemplary embodiment of the invention with reference to the drawings, in which.

DETAILED DESCRIPTION OF EXEMPLARY EMBODIMENTS OF THE INVENTION

Figure 1:
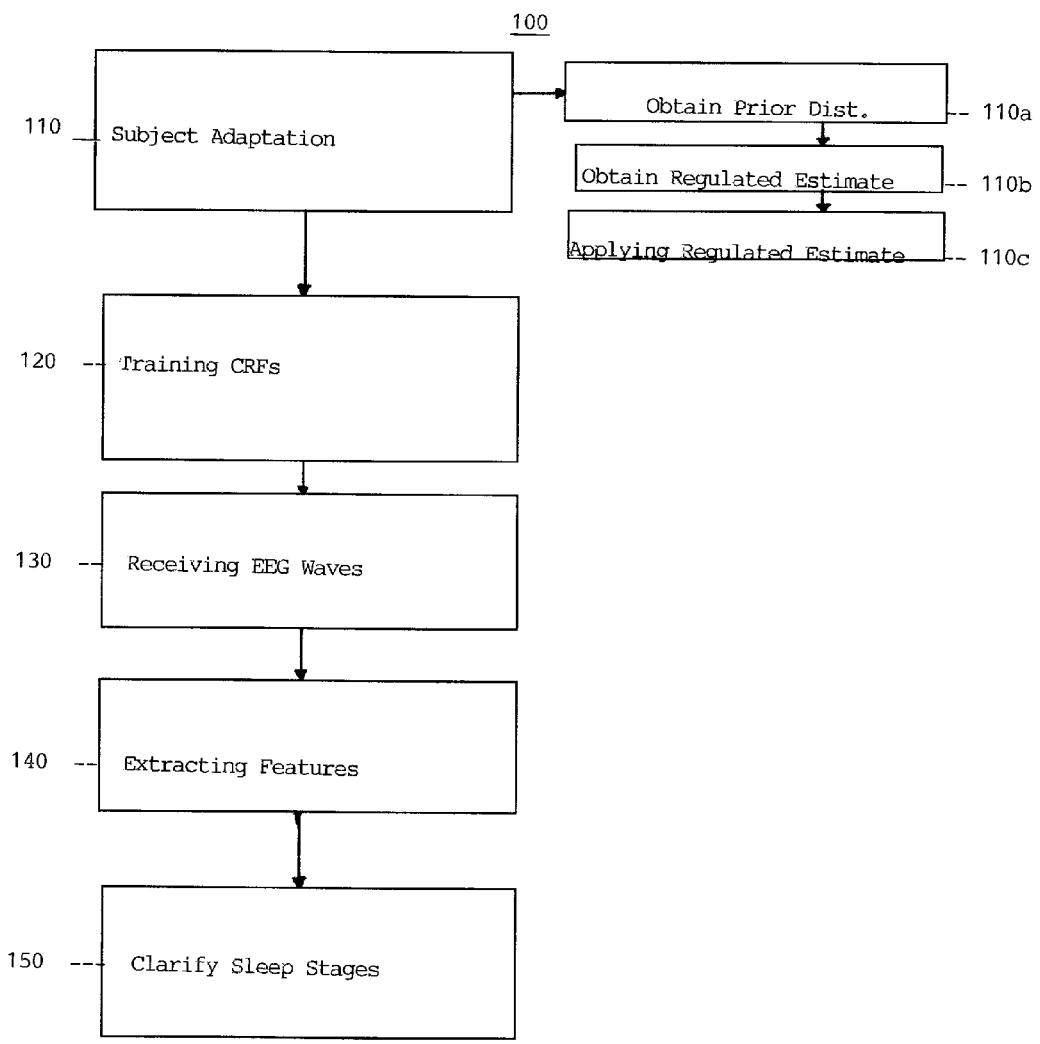
FIG. 1 illustrates a method of subject-adaptive, real-time sleep stage classification to classify electroencephalogram sleep recordings into sleep stages in accordance with an exemplary embodiment of the present invention.
Figure 2:
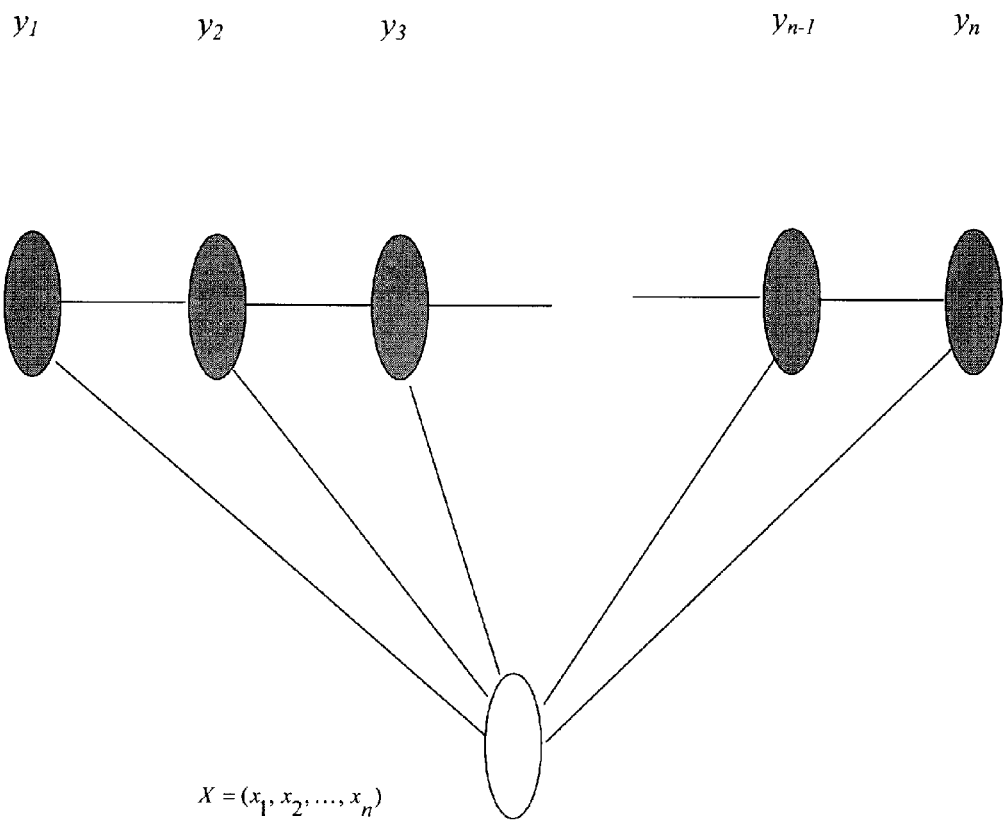
FIG. 2 illustrates a linear-chain CRF.

Referring now to the drawings, and more particularly to FIGS. 1 and 2, there are shown exemplary embodiments of the method and structures according to the present invention.

As indicated above, the present invention uses the concept of CRF. Let X be the observation sequence, and Y be the corresponding label (state) sequence. The CRF is defined (and exemplarily illustrated in FIG. 2) as follows:

Definition. Let G=(V, E) be a graph such that $Y=(y_v)v \in V$, so that Y is indexed by the vertices of G. Then (X, Y) is a conditional random field in case, when conditioned on X, the random variables $y_v$ obey the Markov property with respect to the graph: $P(y_v|X, y_w, w \neq v) = P(y_v|X, y_w, w \sim v)$, where $w \sim v$ means that w and v are neighbors in G.

A special case of CRF is the linear-chain CRF (LCRF), where the graph G is a linear chain so that each $y_i$ has exactly two neighbors: $y_{i-1}$ and $y_{i+1}$. In this case, the distribution of the label sequence Y given the observation sequence X has the following form:

$$p(Y|X) \propto \exp\{\Sigma_{i=1}^{n}[\Sigma_{j=1}^{k_1}\lambda_j f_j(y_{i-1}, y_i, x, i) + \Sigma_{j=1}^{k_2}\mu_j g_j(y_i, X, i)]\}. \tag{1}$$

Here, $f_j$ and $g_j$ are called potential functions. $\lambda_j$ and $\mu_j$ are parameters. The selection of appropriate potential functions is both application-dependent and critical to the success of the CRF method.

The sleep stager of the present invention uses linear-chain CRFs. In this case, $X=(\bar{x}_1, \bar{x}_2, \ldots, \bar{x}_n)$ is the observation sequence, where each element $\bar{x}_i=[x_{i,1}, x_{i,2}, \ldots, x_{i,m}]^T$ is an m-dimensional vector that represents the observed EEG wave signal (possibly after some transformation) at time point i ($1 \leq i \leq n$). $Y=(y_1, y_2, \ldots, y_n)$ is the label sequence. Each $y_i$ ($1 \leq i \leq n$) belongs to the sleep stage space S (e.g., {wake, REM, NREM}) and represents the sleep stage at time point i that needs to be labeled.

The sleep stager of the present invention uses the following two kinds of potential functions, the first one is for $f_j$ and the second one is for $g_j$:

$$1_{y_{i-1}=s} y_{y_i=t}(s, t \in S), \tag{1}$$

$$1_{y_i=1} x_{i,h}(t \in S, 1 \leq h \leq m). \tag{2}$$

Here, the indicator function $$1_{y_i=t} = \begin{cases} 1 & (\text{if } y_i = t) \\ 0 & (\text{if } y_i \neq t) \end{cases}. \text{ For each } i(1 \leq i \leq n),$$

the number of potential functions is $k=|S|^2+|S|m$. Local features are often the most important ones. Hence, at any time point i($1 \leq i \leq n$), the sleep stager focuses on the local observation elements and only consider the first-order term $\bar{x}_i$. In addition, these potential functions are easy to compute, which is important for online classification. In fact, these potential functions can be justified from the statistical mechanics perspective: (1) The term $\exp\{\lambda_{s,t} 1_{y_{i-1}=s} 1_{y_i=t}\}$ can be viewed as the spontaneous transition probability from state s to state t. (2) As discussed below, X is the power spectral density, a quantity associated with energy. Hence, the term $\exp\{\mu_{t,h} 1_{y_i=t} x_{i,h}\}$ can be viewed as an analogy to the Boltzmann factor $P(E) \propto \exp(-\beta E)$, which is related to the probability for a canonical ensemble to be in a state with energy E.

Given the $k=k_1+k_2$ potential functions, parameter estimation (i.e., learning $\lambda_j$'s and $\mu_j$'s from a labeled training data set) and inference making (i.e., given X, computing the most likely Y) in the CRF are performed using the forward-backward dynamic programming and Viterbi algorithms.

The present invention uses a method of subject adaptation. This technique combines the (usually sufficient) training data sequence ($X_{old}$, $Y_{old}$) from several old subjects $s_{old}$ with the (possibly insufficient) training data sequence ($X_{new}$, $Y_{new}$) from a new subject $s_{new}$ to improve the classification accuracy on $s_{new}$. Let $\Theta$ be the column parameter vector of the CRF that contains $\lambda_j$'s and $\mu_j$'s. $L_{old}(\Theta)=\ln p(Y_{old}|X_{old},\Theta)$ and $L_{new}(\Theta)=\ln p(Y_{new}|X_{new},\Theta)$ are the log-likelihood functions for $s_{old}$ and $s_{new}$, respectively. Let $\hat{\Theta}$ denote the maximum-likelihood estimator (MLE) of $\Theta$ on $s_{old}$. A theorem about MLE asserts that $\hat{\Theta}$ asymptotically follows a normal distribution, whose mean vector and covariance matrix are $\Theta$ and $\Sigma=-(\nabla^2 L_{old})^{-1}$, respectively. Here, $\nabla^2 L_{old}$ is the Hessian matrix of $L_{old}(\Theta)$. This can be viewed as a prior of $\Theta$ when we fit the same model to $s_{new}$. The corresponding probability density function is $$p(\Theta) \propto \exp\{-(\Theta-\hat{\Theta})^T \Sigma^{-1} \cdot (\Theta-\hat{\Theta})/2\} = \exp\{(\Theta-\hat{\Theta})^T \cdot \nabla^2 L_{old} \cdot (\Theta-\hat{\Theta})/2\}. \tag{2}$$

From Bayes' theorem, the posterior distribution of $\Theta$ is $$p(\Theta|X_{new}, Y_{new}) \propto p(Y_{new}|X_{new}, \Theta) p(\Theta) \propto \exp\{L_{new}(\Theta) + (\Theta-\hat{\Theta})^T \cdot \nabla^2 L_{old} \cdot (\Theta-\hat{\Theta})/2\}. \tag{3}$$

The gradient of $L_{old}(\Theta)$, $\nabla L_{old}$, can be efficiently computed using a backward-forward dynamic programming method. $\nabla^2 L_{old}$ can be computed numerically by taking difference quotients of $\nabla L_{old}$. Then one can obtain the point estimate $\Theta$ for $s_{new}$ by maximizing $L_{new}(\Theta)+(\Theta-\hat{\Theta})^T \cdot \nabla^2 L_{old} \cdot (\Theta-\hat{\Theta})/2$ (e.g., using the BFGS method).

Each EEG recording is first transformed to capture the embedded, useful information. This process is called feature extraction. The most popular signal processing techniques for feature extraction include wavelet transform, fast Fourier transform, zero-crossing, parametric waveform recognition, etc. The present invention uses an approach based on power spectral properties of the EEG signal. The Thompson multitaper method is applied to 3-second moving window to obtain the localized power spectral density (PSD) with between-window-shift of 2.7 seconds. For each frequency $f$ and each time point i, the logarithm of the PSD is normalized across time to obtain the Z score $z_{f,i}$, where normalization is performed by first subtracting the mean and then dividing by the standard deviation.

For human beings, the method uses m=6 disjoint frequency bands: 0.2 Hz-4 Hz, 4.2 Hz-8 Hz, 8.2 Hz-12 Hz, 12.2 Hz-16 Hz, 16.2 Hz-23 Hz, and 23.2 Hz-29 Hz, which jointly contain 99% of the power of EEG waves. (For birds (e.g., zebra finches), we choose m=4 disjoint frequency bands: 1 Hz-5 Hz, 5.5 Hz-10 Hz, 10.5 Hz-20 Hz, and 20.5 Hz-30 Hz.) The justifications for selecting these frequency bands are as follows. First, the PSD curves of various stages are well separated within these bands. Second, human sleep is characterized into different stages based on the frequency content of the delta-wave (0 Hz-4 Hz), theta-wave (4 Hz-8 Hz), alpha-wave (8 Hz-13 Hz), beta1-wave (13 Hz-22 Hz), and beta2-wave (22 Hz-35 Hz), which are similar to our frequency bands. Hence, the features contained within these bands should provide enough discrimination power for stage classification.

For the jth ($1 \leq j \leq 6$) band, at time point i, let $\tilde{x}_{i,j}$ denote the maximum Z score within this band. That is, $\tilde{x}_{i,j}=\max\{Z_{f,i}$, for all frequencies f in the jth band}. Since occasionally the recording has very large noise caused by movement, we truncate $\tilde{x}_{i,j}$ by $x_{i,j}=\text{sign}(\tilde{x}_{i,j}) \min\{|\tilde{x}_{i,j}|, \Lambda\}$, where $\Lambda=5$.

Vector $\bar{x}_i=[x_{i,1}, x_{i,2}, \ldots, x_{i,m}]^T$ is the transformed observation element at time point i. The classification of the sleep recording is based on the $x_i$'s across time.

FIG. 1 illustrates a method flow chart for an exemplary embodiment of the present invention. The exemplary method 100 of subject-adaptive, real-time sleep stage classification to classify electroencephalogram sleep recordings into sleep stages to determine whether a subject exhibits a sleep disorder, includes performing subject adaptation (step 110) to improve classification accuracy for a new subject with limited training data, training the linear-chain conditional random fields using the training data (step 120), continuously receiving the electroencephalogram waves (step 130), continuously extracting features from the electroencephalogram waves (step 140), and continuously classifying the sleep stages according to extracted features and learned parameters from the linear-chain conditional random fields (step 150). The performing subject adaptation includes using training data from a plurality of old subjects to obtain a prior distribution of conditional random field parameters (110*a*), using the prior distribution of conditional random field parameters in combination with training data for at least one new subject to obtain a regulated estimate of conditional random field parameters (110*b*), and using the regulated estimate of conditional random field parameters to classify the electroencephalogram waves of the at least one new subject to determine whether a subject exhibits a sleep disorder (110*c*).

A typical hardware configuration of an information handling/computer system in accordance with the invention preferably has at least one processor or central processing unit (CPU).

The CPUs are interconnected via a system bus to a random access memory (RAM), read-only memory (ROM), input/output (I/O) adapter (for connecting peripheral devices such as disk units and tape drives to the bus), user interface adapter (for connecting a keyboard, mouse, speaker, microphone, and/or other user interface device to the bus), a communication adapter for connecting an information handling system to a data processing network, the Internet, an Intranet, a personal area network (PAN), etc., and a display adapter for connecting the bus to a display device and/or printer (e.g., a digital printer or the like).

In addition to the system and method described above, a different aspect of the invention includes a computer-implemented method for performing the above method. As an example, this method may be implemented in a computer system environment.

Such a method may be implemented, for example, by operating a computer, as embodied by a digital data processing apparatus, to execute a sequence of computer-readable instructions. These instructions may reside in various types of computer-readable media.

Thus, this aspect of the present invention is directed to a programmed product, comprising computer-readable media tangibly embodying a program of computer-readable instructions executable by a digital data processor incorporating the CPU and hardware above, to perform the method of the invention.

This computer-readable media may include, for example, a RAM contained within the CPU, as represented by the fast-access storage for example. Alternatively, the instructions may be contained in another computer-readable media, such as a magnetic data storage diskette, directly or indirectly accessible by the CPU. Whether contained in the diskette, the computer/CPU, or elsewhere, the instructions may be stored on a variety of computer-readable data storage media, such as DASD storage (e.g., a conventional "hard drive" or a RAID array), magnetic tape, electronic read-only memory (e.g., ROM, EPROM, or EEPROM), an optical storage device (e.g. CD-ROM, WORM, DVD, digital optical tape, etc.), paper "punch" cards, or other suitable computer-readable media including transmission media such as digital and analog and communication links and wireless. In an illustrative embodiment of the invention, the computer-readable instructions may comprise software object code.

While the invention has been described in terms of several exemplary embodiments, those skilled in the art will recognize that the invention can be practiced with modification within the spirit and scope of the appended claims.

Further, it is noted that, Applicants' intent is to encompass equivalents of all claim elements, even if amended later during prosecution.

What is claimed is:

1. A method of subject-adaptive, real-time sleep stage classification to classify electroencephalogram sleep recordings into sleep stages to determine whether a subject exhibits a sleep disorder, comprising:

performing subject adaptation to improve classification accuracy for a new subject with limited training data, said performing subject adaptation comprises using linear-chain conditional random fields and potential functions;

training said linear-chain conditional random fields using said training data;

continuously receiving said electroencephalogram waves;

continuously extracting features from said electroencephalogram waves, said extracting features comprising transforming each of said electroencephalogram waves to capture information embedded in said electroencephalogram waves, said extracting features comprises extracting features from four disjoint frequency bands, said four disjoint frequency bands consisting of a first band within a range of 1 $H_z$-5 $H_z$, a second band within a range of 5.5 $H_z$-10 $H_z$, a third band with a range of 10.5 $H_z$-20 $H_z$, and a fourth band within a range of 20.5 $H_z$-30 $H_z$; and continuously classifying the sleep stages according to extracted features and learned parameters from said linear-chain conditional random fields, wherein said performing subject adaptation comprises:

using training data from a plurality of old subjects to obtain a prior distribution of conditional random field parameters;

using said prior distribution of conditional random field parameters in combination with training data for at least one new subject to obtain a regulated estimate of conditional random field parameters; and using said regulated estimate of conditional random field parameters to classify said electroencephalogram waves of said at least one new subject to determine whether a subject exhibits a sleep disorder, wherein said continuously extracting features comprises obtaining a localized power spectral density of said electroencephalogram waves.

* * * * *